United States Patent
Alfano et al.

(10) Patent No.: US 7,218,959 B2
(45) Date of Patent: May 15, 2007

(54) HYBRID-DUAL-FOURIER TOMOGRAPHIC ALGORITHM FOR A FAST THREE-DIMENSIONIAL OPTICAL IMAGE RECONSTRUCTION IN TURBID MEDIA

(75) Inventors: Robert R. Alfano, Bronx, NY (US); Wei Cai, Bronx, NY (US)

(73) Assignee: Research Foundation of City University, New York, NY (US)

( * ) Notice: Subject to any disclaimer, the term of this patent is extended or adjusted under 35 U.S.C. 154(b) by 589 days.

(21) Appl. No.: 10/456,264

(22) Filed: Jun. 5, 2003

(65) Prior Publication Data

US 2004/0030255 A1    Feb. 12, 2004

Related U.S. Application Data

(60) Provisional application No. 60/386,054, filed on Jun. 5, 2002.

(51) Int. Cl.
*A61B 6/00*    (2006.01)
(52) U.S. Cl. .................. 600/476; 600/310; 600/473
(58) Field of Classification Search ............. 600/476, 600/473; 250/495.1, 316.1; 356/303
See application file for complete search history.

(56) References Cited

U.S. PATENT DOCUMENTS

| | | | |
|---|---|---|---|
| 5,931,789 A | | 8/1999 | Alfano et al. |
| 6,108,576 A | | 8/2000 | Alfano et al. |
| 6,205,353 B1 | | 3/2001 | Alfano et al. |
| 6,615,063 B1 | * | 9/2003 | Ntziachristos et al. ...... 600/312 |
| 2001/0032053 A1 | * | 10/2001 | Hielscher et al. ............. 702/22 |
| 2004/0092824 A1 | * | 5/2004 | Stamnes et al. ............ 600/473 |

OTHER PUBLICATIONS

Christian Hansen, "The truncated SVD as a method for regularization", BIT 27 (1987) pp. 534-553.*
Golub et al., "Generalized Cross-Validation as a method for choosing a good ridge parameter", Technometrics, vo.21, No. 2, pp. 215-223 (1979).*
Jiang et al., "Frequency-domain optical image reconstruction in turbid media: an experimental study of single-target detectability", Applied Optics vol. 36, No. 1, pp. 52-63 (1997).
O'Leary et al., "Experimental images of heterogeneous turbid media by frequency-domain diffusing-photon tomography", Optics Letters, vol. 20, No. 5, pp. 426-428 (1995).
Fantini et al., "Assessment of the size, position, and optical properties of breast tumors in vivo by noninvasive optical methods", Applied Optics, vol. 37, No. 10, pp. 1982-1989 (1998).

(Continued)

*Primary Examiner*—Eleni Mantis Mercader
*Assistant Examiner*—Jacqueline Cheng
(74) *Attorney, Agent, or Firm*—Cohen Pontani Lieberman & Pavane LLP

(57) ABSTRACT

A reconstruction technique for reducing computation burden in the 3D image processes, wherein the reconstruction procedure comprises an inverse and a forward model. The inverse model uses a hybrid dual Fourier algorithm that combines a 2D Fourier inversion with a 1D matrix inversion to thereby provide high-speed inverse computations. The inverse algorithm uses a hybrid transfer to provide fast Fourier inversion for data of multiple sources and multiple detectors. The forward model is based on an analytical cumulant solution of a radiative transfer equation. The accurate analytical form of the solution to the radiative transfer equation provides an efficient formalism for fast computation of the forward model.

17 Claims, 8 Drawing Sheets

OTHER PUBLICATIONS

Zhu et al., "Iterative total least-squares image reconstruction algorithm for optical tomography by the conjugate gradient method", J. Opt. Soc. Am. A, vol. 14, No. 4, pp. 799-807 (1997).

Li et al., "Diffraction tomography for biochemical imaging with diffuse-photon density waves", Optics Letters, vol. 22, No. 8, pp. 573-575 (1997).

C. L. Matson and H. Liu, "Analysis of the forward problem with diffuse photon density waves in turbid media by use of a diffraction tomography model", J. Opt. Soc. Am. A, vol. 16, No. 3, pp. 455-466 (1999).

C. L. Matson and H. Liu, "Backpropagation in turbid meda", J. Opt. Soc. Am. A, vol. 16, No. 6, pp. 1254-1265 (1999).

Cai et al., "Optical tomographic image reconstruction from ultrafast time-sliced transmission measurements", Applied Optics, vol. 38, No. 19, pp. 4237-4246 (1999).

Xu et al., "Time-resolved fourier optical diffuse tomography", J. Opt. Soc. Am. A, vol. 18, No. 7, pp. 1535-1542 (2001).

Cai et al., "Three dimensional image reconstruction in highly scattering turbid media", SPIE, vol. 2979, pp. 241-248.

Cai et al., Cumulant solution of the elastic Boltzmann transport equation in an infinite uniform medium, Physical Review E, vol. 61, No. 4, pp. 3871-3876 (2000).

Cai et al., "Analytical solution of the elastic Boltzmann transport equation in an infinite uniform medium using cumulant expansion", J. Phys. Chem. B., vol. 104, pp. 3996-4000 (2000).

Cai et al., "Analytic solution of the polarized photon transport equation in an infinite uniform medium using cumulant expansion", Physical Review E, vol. 63, pp. 016606-1-016606-10 (2000).

Cai et al., "Photon-transport forward model for imaging in turbid media", Optics Letters, vol. 26, No. 14, pp. 1066-1068 (2001).

Gayen et al., "Near-infrared laser spectroscopic imaging: A step towards diagnostic optical imaging of human tissues", Lasers in the Life Sciences, vol. 8. pp. 187-198.

Christian Hansen, "The truncated SVD as a method for regularization", BIT 27 (1987) pp. 534-553.

Golub et al., "Generalized Cross-Validation as a method for choosing a good ridge parameter", Technometrics, vo. 21, No. 2, pp. 215-223 (1979).

* cited by examiner

HYBRID-DUAL-FOURIER TOMOGRAPHIC ALGORITHM FOR A FAST THREE-DIMENSIONIAL OPTICAL IMAGE RECONSTRUCTION IN TURBID MEDIA

RELATED APPLICATIONS

This application claims priority from U.S. Provisional Patent Application Ser. No. 60/386,054, which was filed on Jun. 5, 2002.

STATEMENT AS TO RIGHTS TO INVENTIONS MADE UNDER FEDERALLY-SPONSORED RESEARCH AND DEVELOPMENT

This invention was made, in part, with Government support awarded by National Aeronautics and Space Administration (NASA), and the US Army Medical Research and Materiel Command (USAMRMC). The Government may have certain rights in this invention.

BACKGROUND OF THE INVENTION

1. Field of the Invention

The present invention teaches a novel hybrid-dual-Fourier inverse algorithm for fast three dimensional (3D) tomographic image reconstruction of objects in highly scattering media using measured data from multiple sources and multiple detectors. This algorithm can be used for noninvasive screening, detection, and diagnosis of cancerous breast and prostate lesions, and for locating hidden objects in high scattering media, such as planes, tanks, objects within an animal or human body, or through cloud, fog, or smoke, mines under turbid water, and corrosion under paint.

2. Description of the Related Art

Turbid media blur and make objects inside difficult to be detected. Light propagation is diffusive, making the object inside not detectable using conventional imaging methods. In highly scattering media, when the object is located inside a turbid medium with depth greater than 10 scattering length, the object cannot be seen easily using ballistic light. It is also difficult to use time-gated transillumination technique to image objects in turbid media with $L/I_s>20$, with L the size of the medium and $I_s$ the scattering length, because of photon starvation of the ballistic light. To overcome this difficulty one uses the image reconstruction of light in the medium to get three-dimensional image. This requires understanding of how light travels in the turbid media, and an appropriate inverse algorithm. Objects, such as tumors, aircraft, and corrosion in highly scattering media can be imaged using the novel image algorithm in turbid media. Turbid media include human tissue, cloud, and under paint.

Early detection and diagnosis of breast and prostate cancers is essential for effective treatment. X-ray mammography, the modality commonly used for breast cancer screening, cannot distinguish between malignant and benign tumors, and is less effective for younger women with dense fibrous breasts. If a tumor is suspected from a x-ray mammogram, a biopsy that requires invasive removal of tissue from the suspect region need be performed to determine if the tumor is benign or malignant. In a majority of the cases, the biopsy turns out to be negative, meaning the tumor is benign. Besides being subject to an invasive procedure, one has to wait an agonizing period until the biopsy results are known. A breast cancer screening modality that does not require tissue removal, and can provide diagnostic information is much desired.

Prostate cancer has a high incidence of mortality for men. Every year, nearly 180,000 new prostate cancer cases are diagnosed, and prostate cancers in U.S annually cause about 37,000 deaths. The developed cancers may spread to the lymph nodes or bones causing persistent and increasing pain, abnormal function, and death. The detection and treatment of early small prostate cancers are most important to prevent death attributable to prostate cancer. Current noninvasive approaches to detect the early prostate include the ultrasound, MRI and CT imaging, which have poor spatial resolution and contrast. Other means, such as needle biopsy, are invasive. Optical image as disclosed here can be used to image tumors in prostate.

Optical tomography is being developed as a noninvasive method that uses nonionizing near-infrared (NIR) light in the 700–1500 nm range to obtain images of the interior of the breast and prostate. Tissues scatter light strongly, so a direct shadow image of any tumor is generally blurred by scattered light. A technique, known as inverse image reconstruction (IIR), may help circumvent the problem of scattering. An IIR approach uses the knowledge of the characteristics of input light, measured distribution of light intensity that emerges from the illuminated breast and prostate, and a theoretical model that describes how light propagates through breast and prostate to construct an image of the interior of breast and prostate. Back scattering and transmission geometries are used for breast. For prostate, backscattering geometry is more suitable. The image reconstruction methods can also be used to image objects in hostile environments of smoke, cloud, fog, ocean, sea, and to locate corrosion under paint.

Although the problem has received much attention lately, that development of optical tomography has been slow. One of main difficulties is lack of an adequate algorithm for inversion image reconstruction, which is able to provide a 3D image in reasonable computing times. Recent algorithms and methods have been developed to solve the inverse problem in order to produce images of inhomogeneous medium, including finite-element solutions of the diffusion equation and iterative reconstruction techniques, modeling fitting, least-square-based and wavelet based conjugate-gradient-decent methods. Examples of references which disclose this technique include: H. B. Jiang et al, "Frequency-domain optical image reconstruction in turbid media: an experimental study of single-target detectability," Appl. Opt. Vol. 36 52–63 (1997); H. B. O'Leary et al, "Experimental image of heterogeneous turbid media by frequency-domain diffusing-photon tomography," Opt. Lett. Vol. 20, 426–428 (1995); S. Fantini et al, "Assessment of the size, position, and optical properties of breast tumors in vivo by noninvasive optical methods," Appl. Opt. Vol 36, 170–179 (1997); W. Zhu et al "Iterative total least-squares image reconstruction algorithm for optical tomography by the conjugate gradient method," J. Opt. Soc. Am. A Vol. 14 799–807 (1997), all of which are incorporated herein by reference. These methods take significantly long computing time for obtaining a 3D image to be of use in clinical applications and other detections. These methods require a linearly or non-linearly inverse of a group of equations, which have huge unknown augments that equal to the number of voxels in a 3D volume (a voxel is a small volume unit in 3D volume, and corresponds to a pixel in 2D plane).

Using a Fourier transform inverse procedure can greatly reduce computing time. Examples of references that disclose this technique include: X. D. Li et al, "Diffraction tomography for biomedical imaging with diffuse-photon density waves," Opt. Lett. Vol. 22, 573–575 (1997); C. L. Matson et al, "Analysis of the forward problem with diffuse photon density waves in turbid media by use of a diffraction tomography model," J. Opt. Soc. Am. A Vol. 16, 455–466 (1999); C. L. Matson et al, "Backpropagation in turbid media,", J. Opt. Soc. Am. A Vol. 16, 1254–1265 (1999), all of which are incorporated herein by reference. In the Fourier transform procedure, the experimental setup should satisfy the requirement of spatial translation invariance, which restricts, up to now, use of a single laser source (a point source or a uniformly distributed plane source) with a 2D plane of detectors in parallel (transmission or reflection) geometry. This type of experimental setup can acquire only a set of 2D data for continuous wave (CW) or frequency-domain tomography, which is generally not enough for reconstruction of a 3D image, resulting in uncertainty in the depth of the objects in 3D image.

To overcome this difficulty of lack of enough data for 3D image in tomography using a Fourier procedure, we have in the past developed algorithms to acquire time-resolved optical signals, which provides an additional 1D (at different times) of acquired data, so 3D image reconstruction can be performed. Examples of references which disclose this technique include: R. R. Alfano et al: "Time-resolved diffusion tomographic 2D and 3D imaging in highly scattering turbid media," U.S. Pat. No. 5,931,789, issued Aug. 3, 1999; U.S. Pat. No. 6,108,576, issued Aug. 22, 2000; W. Cai et al: "Optical tomographic image reconstruction from ultrafast time-sliced transmission measurements," Appl. Optics Vol. 38, 4237–4246 (1999); M. Xu et al, "Time-resolved Fourier optical diffuse tomography", JOSA A Vol. 18 1535–1542 (2001). Schotland and Markel developed inverse inversion algorithms using diffusion tomography based on the analytical form of the Green's function of frequency-domain diffusive waves, and point-like absorbers and scatterers. Examples of references which disclose this technique include: V. A. Markel, J. C. Schotland, "Inverse problem in optical diffusion tomography. I Fourier-Laplace inversion formulas", J. Opt. Soc. Am. A Vol. 18, 1336 (2001); V. A. Markel, J. C. Schotland, "Inverse scattering for the diffusion equation with general boundary conditions", Phys. Rev. E Vol. 64, 035601 (2001), all of which are incorporated herein by reference.

From the viewpoint of data acquisition in parallel geometry, however, it is desirable to use a 2D array of laser sources, which can be formed by scanning a laser source through a 2D plane, and a 2D plane of detectors, such as a CCD camera or a CMOS camera. Each illumination of laser source produces a set of 2D data on the received detectors. For CW or frequency-modulated laser source, this arrangement can produce a set of (2D, 2D)=4D data in a relatively short acquisition time, with enough accuracy and at reasonable cost. When time-resolved technique is applied using a pulse laser source, a set of 5D data can be acquired. In these cases the inverse problem of 3D imaging is over-determined, rather than under-determined for the case of using a single CW or frequency domain sources, and thus produces a much more accurate 3D image.

The key point is how to develop an algorithm, which is scientifically proper, and runs fast enough to produce a 3D image, so it can be realized for practical clinical applications and other field applications.

SUMMARY OF THE INVENTION

One object of the present invention is to teach and provide an inverse algorithm for fast three dimensional tomographic image reconstruction using a hybrid-dual-Fourier inverse method suitable for experimental arrangements of multiple sources and multiple detectors in parallel (transmission or backscattering) geometries for either CW, frequency-domain, and/or time-resolved approaches.

Another object of the present invention is to teach and provide an inverse algorithm for three dimensional tomographic image reconstruction using a hybrid-dual-Fourier inverse method based on experimental arrangements of multiple sources and multiple detectors in cylindrical geometries for either CW, frequency-domain, and/or time-resolved approaches.

A further object of the present invention is to teach and provide a novel hybrid-dual-Fourier mathematical method as an extension of the standard Fourier deconvolution method, applied to any kind of N-dimensional dual deconvolution problems where measurement data depend on two variables, and weight function satisfy the condition of translation invariance for each variable in a M-dimensional subspace.

Yet another object of the present invention is to teach and provide an accurate analytical solution of the Boltzmann photon transport equation in a uniform medium to serve as background Green's function in the forward physical model for the tomography method of the present invention.

Still another object of the present invention is to teach and provide a tomographic method using laser sources with different wavelengths for producing an internal map of a specific material structure in a turbid medium.

One other object of the present invention is to teach and provide experimental designs for using hybrid-dual-Fourier tomography for detecting cancer and to develop an optical tomography imaging system.

Additional objects, as well as features and advantages, of the present invention will be set forth in part in the description which follows, and in part will be obvious from description or may be learned by practice of the invention.

In accordance with one embodiment of the present invention, a method for imaging an object in a turbid medium comprises the steps of:

(a) directing an incident light from a source onto the turbid medium to obtain a plurality of emergent waves from the turbid medium;

(b) determining the intensity data of at least part of the emergent waves by a plurality of detectors;

(c) repeating the steps of a) and b) by placing the source of incident light at different positions until data acquisition is substantially complete; and (d) processing the intensity data by using an image reconstruction algorithm including a forward physical model and an inverse algorithm, to inversely construct a three dimensional image of the object in the turbid medium, where the inverse algorithm is a hybrid dual Fourier tomographic algorithm.

In accordance with another embodiment of the present invention, a system for imaging an object in a turbid medium comprises:

(a) a source for directing an incident wave onto the turbid medium to obtain a plurality of emergent waves from the turbid medium;

(b) a plurality of detectors disposed along the propagation paths of at least part of the emergent waves for determining the intensity data of the emergent waves; and (c) a data processor connected to the detectors to process the obtained intensity data and produce a three dimensional image of the object in the turbid media, where the data processor is programmed to execute an inverse algorithm based on a forward physical model to process the intensity.

The present invention is directly related to an optical tomographic method for imaging hidden objects in highly scattering turbid media. In one aspect of the present invention, a method for imaging objects in a highly scattering turbid medium in parallel geometry includes the steps of: using a light source in visible and/or infrared spectral region, step by step, scanning through a two dimensional (2D) array, to illuminate a highly scattering medium; in each scanning step, to acquire signals of transmitted or backscattered light emergent from the medium received by a two dimensional (2D) array of detectors, such as CCD camera or CMOS camera; and applying a novel hybrid-dual Fourier inverse algorithm to form a three dimensional image of the objects in the highly scattering turbid medium. FIG. 1 schematically shows the experimental setup in parallel geometry used for the teaching presented here.

Preferably, a novel hybrid-dual-Fourier inverse algorithm is developed based on the present inventor's discovery, that by performing a dual 2D Fourier transform upon both arguments related to the source positions and the detector positions, and using a hybrid linear transform, 3D tomography can be realized for use of multiple sources and multiple detectors. The main concept is as follows. A linear forward model describing light migration through an inhomogeneous scattering medium with parallel geometry, based on the Born approximation, either for CW, frequency domain, and/or time-resolved approaches, can be written as:

$$Y(\vec{r}_d, \vec{r}_s, z_d, z_s) = \int d\vec{r} \, dz \, W(\vec{r}_d - \vec{r}, \vec{r}_s - \vec{r}, z, z_d, z_s) X(\vec{r}, z), \quad (1)$$

where $\vec{R} = (\vec{r}, z)$ denotes the position of a voxel inside turbid medium; $\vec{r}$ is (x, y) coordinates; $\vec{R}_s = (\vec{r}_s, z_s)$ denotes the position of a source; $\vec{R}_d = (\vec{r}_d, z_d)$ denotes the position of a detector. In equation (1), $Y(\vec{r}_d, \vec{r}_s, z_d, z_s)$ is the measured change of light intensity, which incident from a source at $\vec{R}_s$ and received by a detector at $\vec{R}_d$. The word "change" refers to the difference in intensity compared to that received by the same detector, from the same source, but light passing through a homogeneous background medium; $X(\vec{r}, z)$ is the change of the optical parameters inside turbid medium, in particular, it means change of the absorption coefficient $\mu_a$ and the reduced scattering coefficient $\mu_s'$ in diffusion tomography. $W(\vec{r}_d - \vec{r}, \vec{r}_s - \vec{r}, z, z_d, z_s)$ is the weight function, which is function of $\vec{r}_d - \vec{r}$ and $\vec{r}_s - \vec{r}$ at (x, y) plane, because of parallel geometry, and the translation invariance of the Green's function in a homogeneous background medium. Here, we do not specify what form of the weight function; it can be an expression of the diffusion forward model, either for CW, Frequency domain, and/or time-resolved cases, or one based on the cumulant analytical solution of the radiative transfer equation we recently developed.

The inverse problem is to determine value of X from known measured data Y. The common understanding is that since the weight function now is related to three positions: $\vec{r}_d$, $\vec{r}_s$, and $\vec{r}$, translation invariance cannot be simultaneously satisfied, hence, it is difficult to performing Fourier inversion when both $\vec{r}_d$ and $\vec{r}_s$ are taken as variable. In the following, we make a dual 2D Fourier transform $\int d\vec{r}_s d\vec{r}_d e^{i\vec{q}_s \vec{r}_s} e^{i\vec{q}_d \vec{r}_d}$ on equation (1), and obtain that $$\hat{Y}(\vec{q}_d, \vec{q}_s, z_d, z_s) = \int dz \hat{W}(\vec{q}_d, \vec{q}_s, z, z_d, z_s) \hat{X}(\vec{q}_d + \vec{q}_s, z), \quad (2)$$

where $\hat{Y}$, $\hat{X}$, and $\hat{W}$ are the corresponding Fourier space quantities in equation (1).

Equation (2) seems most difficult to be used for performing the Fourier inverse reconstruction because the arguments of $\hat{X}$ are different from that of $\hat{Y}$ and $\hat{W}$. To remove this complexity, we perform a linear hybrid transform of the detector's and source's spatial frequency coordinates:

$$\vec{u} = \vec{q}_d + \vec{q}_s$$

$$\vec{v} = \vec{q}_d - \vec{q}_s, \quad (3)$$

that leads to the following formula:

$$\tilde{Y}(\vec{u}, \vec{v}, z_d, z_s) = \int dz \tilde{W}(\vec{u}, \vec{v}, z, z_d, z_s) \tilde{X}(\vec{u}, z), \quad (4)$$

where $\tilde{Y}$, $\tilde{X}$, and $\tilde{W}$ are, respectively, $\hat{Y}$, $\hat{X}$, and $\hat{W}$ as functions of $\vec{u}$ and $\vec{v}$.

FIG. 2 schematically explains the linear hybrid transform in equation (3), using an example of 6×6 lattices, from ($q_d$, $q_s$) coordinates to (u, v) coordinates. Note that the periodic property of lattices in the Fourier space is used, for example, $\hat{Y}(u=2, v=4) = \hat{Y}(q_d=3, q_s=5)$ as shown in FIG. 2. This figure shows that $\hat{Y}$ and $\hat{W}$ at each node in (u, v) coordinates can be obtained, respectively, from $\hat{Y}$ and $\hat{W}$ at the corresponding node in ($q_d$, $q_s$) coordinates without any algebraic manipulation.

The hybrid transform equation (3) is a key, which makes the inverse reconstruction much easier to be performed. For each value $\vec{u}$, equation (4) leads to an over-determining 1D problem for inverse reconstruction, namely, to determine a 1D unknown value of $\tilde{X}(\vec{u}, z)$ from known 2D data of $\tilde{Y}(\vec{u}, \vec{v})$ for each $\vec{u}$. Detail of this 1D procedure is described in the section of "detailed description of preferred embodiments." This task is much easier than direct inversion of equation (1), which is a 3D inverse problem. After $\tilde{X}(\vec{u}, z)$ for all $\vec{u}$ are obtained, a 2D inverse Fourier transform produces $X(\vec{r}, z)$, which is the 3D image of optical parameters of the body.

Using this algorithm to perform an inverse reconstruction of 3D image of breast tissue with enough fine resolution (for example, 32×32×20 voxels) only takes a few minutes on a personal computer.

Preferably, the hybrid-dual-Fourier inversion method can be used for turbid medium of substantially the cylindrical geometry, with an arbitrary shape of the (x, y) cross section, for 3D tomographic image reconstruction. FIG. 3 schematically shows the experimental setup in the cylindrical geometry. Under this geometry, an algorithm using single-Fourier inversion was developed. Examples of references which disclose this technique include: Cai et al. "Three dimensional image reconstruction in high scattering turbid media," SPIE 2979, p241–248 (1997), which are incorporated herein by reference. This algorithm limits to apply to the cases that the sources and the detectors are located at the same z plane, which restricts acquiring data. The following invention provides a hybrid-dual-Fourier inverse approach for cylinder geometry to remove the above-mentioned limitation, so more data can be acquired for 3D tomography. The linear forward model in the cylinder geometry is given by $$Y(\vec{r}_d, \vec{r}_s, z_d, z_s) = \int d\vec{r} \, dz \, W(\vec{r}_d, \vec{r}_s, \vec{r}; z_d-z, z_s-z) X(\vec{r}, z), \quad (5)$$

where $W(\vec{r}_d, \vec{r}_s, \vec{r}; z_d-z, z_s-z)$ is the weight function, which is function of $z_d-z$ and $z_s-z$ because of cylinder geometry (assuming infinite z length) and the translation invariance of the Green's function in a homogeneous background medium.

We make a dual 1D (along z direction) Fourier transform $\int dz_d dz_s e^{iq_d z_d} e^{iq_s z_s}$ on equation (5), and obtain that $$\hat{Y}(q_d, q_s, \vec{r}_d, \vec{r}_s) = \int d\vec{r} \, \hat{W}(q_d, q_s, \vec{r}, \vec{r}_d, \vec{r}_s) \hat{X}(q_d+q_s, \vec{r}), \quad (6)$$

where $\hat{Y}$, $\hat{X}$, and $\hat{W}$ are the corresponding Fourier space quantities in equation (5). We further perform a linear hybrid transform (1D) of the detector's and source's spatial frequency coordinates:

$$u = q_d + q_s$$

$$v = q_d - q_s, \quad (7)$$

that leads to:

$$\tilde{Y}(u, v, \vec{r}_d, \vec{r}_s) = \int d\vec{r} \, \tilde{W}(u, v, \vec{r}_d, \vec{r}_s; \vec{r}) \tilde{X}(u, \vec{r}), \quad (8)$$

where $\tilde{Y}$, $\tilde{X}$, and $\tilde{W}$ are, respectively, $\hat{Y}$, $\hat{X}$, and $\hat{W}$ as functions of u and v. For each value of u, the above-mentioned equation leads to a over-determining 2D problem for inverse reconstruction, namely, to determine a 2D unknown value of $\tilde{X}(u, \vec{r})$ from known 3D data of $\tilde{Y}(u, v, \vec{r}_d, \vec{r}_s)$ for each u. This 3D-2D determination enhances accuracy of 3D image comparing to 2D—2D determination in the single-Fourier transform inversion. After $\tilde{X}(u, \vec{r})$ for all u are obtained, a 1D inverse Fourier transform produces $X(\vec{r}, z)$, which is the 3D image of optical parameters.

Preferably, the formula of the hybrid-dual-Fourier approach, equation (1) through equation (4), can be regarded a pure mathematical method to solve a N-dimensional dual deconvolution problem as an extension of the standard Fourier deconvolution method. In a N dimensional space, a deconvolution problem is defined by equation (1), where $\vec{R} = (\vec{r}, z)$ with $\vec{r}$ in a M subspace and z in a N-M subspace; $Y(\vec{r}_d, \vec{r}_s, z_d, z_s)$ is the measurement data which depend on both $\vec{R}_s = (\vec{r}_s, z_s)$ and $\vec{R}_d = (\vec{r}_d, z_d)$. $X(\vec{r}, z)$ is the quantity that should be determined by deconvolution. $W(\vec{r}_d - \vec{r}, \vec{r}_s - \vec{r}, z, z_d, z_s)$ is the weight function, which is function of $\vec{r}_d - \vec{r}$ and $\vec{r}_s - \vec{r}$ at M-dimensional subspace.

The approach described from equation (1) through equation (4), hence, can be applied to many other applications that lead to the form of equation (1). In this form, the sources can be light, X-ray, microwave, sound, electrons, particles, mechanical vibration, etc; the detectors can be any type of sensors for receiving light, X-ray, microwave, sound, electricity, mechanical signals, etc; the "space" can be positions, times, wavelength spectrum, vibration modes, etc. Several examples are as follows: (1) using electrons from a linear electron accelerator through a cargo to detect merchandise inside cargo in the custom; (2) using sound to detect mine vertical distribution under ground; (3) using pressure vibration on the surface of a material to detect the elastic coefficients inside the body. In the abovementioned and other examples, the source (electrons, sound, vibration, etc.) can be scanned on a 2D surface, and sensors can be arranged on the transmission and/or back-reflect 2D surface. The novel hybrid-dual-Fourier inverse algorithm can be applied in these cases for fast 3D imaging.

Preferably, an accurate analytical solution of the Boltzmann photon transport equation in an infinite uniform medium, first derived by the inventors, is combined to the above-mentioned inverse algorithm to provide more accurate forward model than the diffusion forward model. Examples of references which disclose this technique include: R. R. Alfano et al., "Time-resolved optical backscattering tomographic image reconstruction in scattering media", U.S. Pat. No. 6,205,353 issued Mar. 20, 2001; W. Cai, et al., "Cumulant solution of the elastic Boltzmann transport equation in an infinite uniform medium", Phys. Rev. E. 61 3871 (2000); W. Cai, et al., "Analytical solution of the elastic Boltzmann transport Equation in an infinite uniform medium using cumulant expansion", J. Phys. Chem. B104 3996 (2000); W. Cai, et al., "Analytical solution of the polarized photon transport equation in an infinite uniform medium using cumulant expansion," Phys. Rev. E 63 016606 (2001); M. Xu et al., "Photon-transport forward model for imaging in turbid media," Opt. Lett. 26, 1066–1068 (2001), which are incorporated herein by reference. The detailed description is given in the section of "detailed description of preferred embodiments."

In addition, this method can be used to determine the local material structure by distinguishing different values of optical parameters obtained by using different light wavelengths. Water, blood, and fat have different scattering and absorption parameters at different wavelengths in NIR region. Other biological materials, such as cancer, precancerous, and benign tissue will have different value of these optical parameters (scattering and absorption). For example, assume that cancer has the absorption and scattering parameters at a wavelength $\lambda_1$ different from that at a wavelength $\lambda_0$. When two sources are used having respective wavelengths $\lambda_0$ and $\lambda_1$, where $\lambda_0$ is a non-characteristic wavelength, the difference of their absorption coefficients $\mu_a(r, \lambda_1) - \mu_a(r, \lambda_0)$ and the scattering coefficients $\mu_s(r, \lambda_1) - \mu_s(r, \lambda_0)$ can be obtained by inverse computation. This process provides a significantly clearer image map of fat location by eliminating the background values. This procedure can yield maps of water, fat, blood, and calcification, even possibly cancer, using different $\lambda$.

Other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims. It should be further understood that the drawings are not necessarily drawn to scale and that, unless otherwise indicated, they are merely intended to conceptually illustrate the structures and procedures described herein.

DETAILED DESCRIPTION OF THE PRESENTLY PREFERRED EMBODIMENTS

Figure 4:
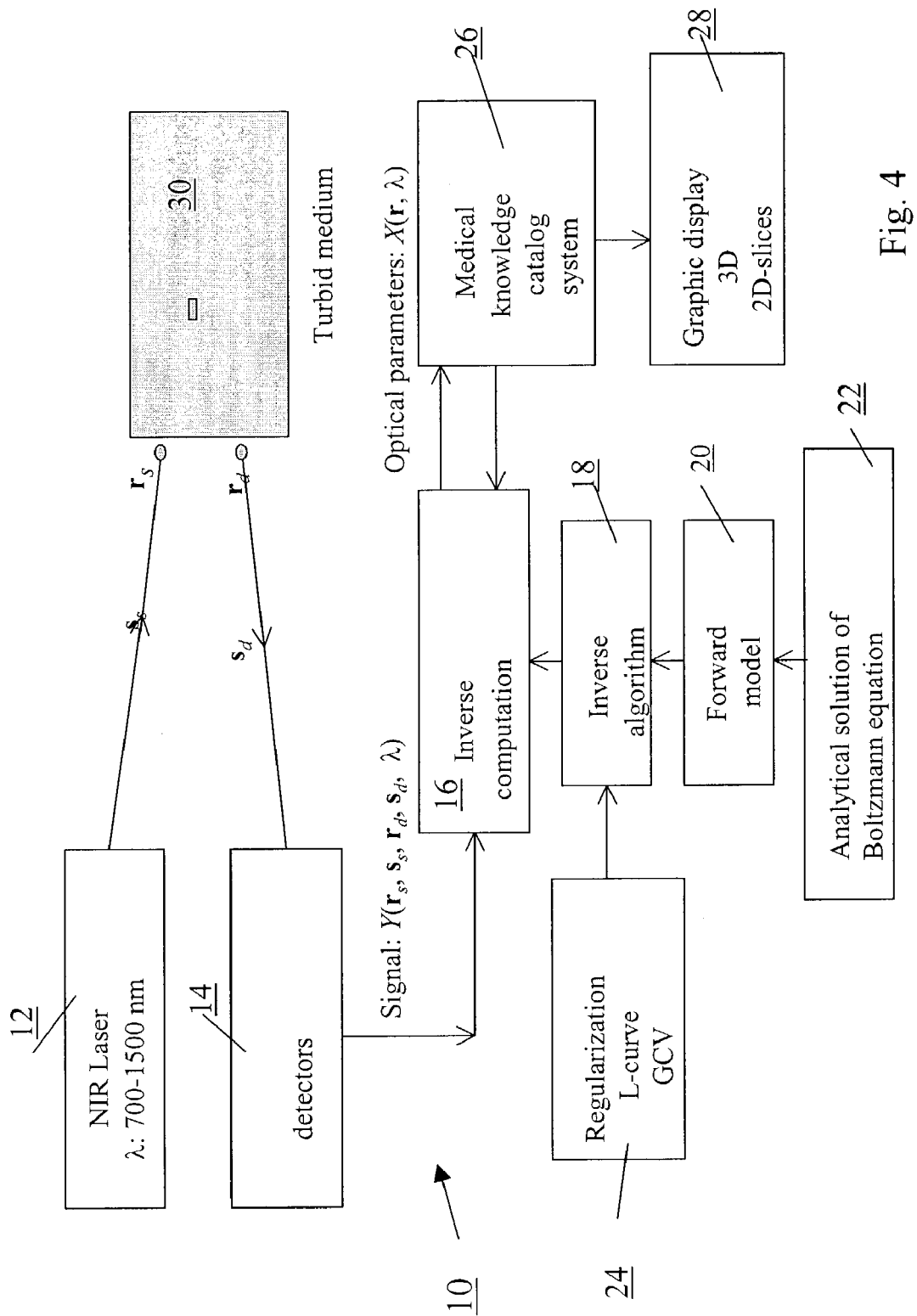
FIG. 4 is a block/flow diagram of an optical tomography system/process in accordance with an embodiment of the present invention.

The present invention is directed to novel optical tomographic system and method for imaging hidden objects in highly scattering turbid media. Referring now to FIG. 4, a block diagram illustrates an optical tomography system in accordance with one aspect of the present invention. It is to be understood that the block diagram depicted in FIG. 4 may also be considered as a flow diagram of a method for imaging objects in turbid media in accordance with the present invention. The system 10 includes an illumination source 12, step by step, shining (direct scanning or using optical fiber) through a two-dimensional array on the plane surface of the turbid medium 30 in parallel geometry, or through around the cylinder surface of the turbid medium 30 in cylinder geometry, and illuminating the turbid medium 30. The illumination source 12 is a laser that emits a continuous wave, or a frequency-modulated light, or ultrashort light pulses (e.g., fsec, psec, and nsec pulses) having wavelengths in the range of about 700 to 1500 nm so as to obtain deep penetration of the turbid medium 30 (such as breast, prostate, brain tissue, and cloud etc.). The laser source may include any conventional laser such as a semiconductor laser, a Ti:Sapphire laser, a $Cr^{4+}$ Forsterite laser, a $Cr^{4+}$ YAG lasers, and a $Cr^{4+}$—$Ca_2GeO_3$ (CUNYITE), a Nd:YAG laser.

A plurality of detectors 14 located at the transmitted plane surface or the backscattering plane surface of the turbid medium in parallel geometry, or located around cylinder surface of the turbid medium in cylinder geometry, are provided for acquiring signals of scattered light emergent from the turbid medium 30 for each shine of laser source. The detectors 14 are implemented CCD (charge coupled device) system or a group of fiber-detectors, and in the case of time-resolved measurement a time gating Kerr or intensified CCD is used for detecting pico-second time slicing signals. The light signals ("intensity data"), which are received by detectors 14, are intensity as functions of the position of the source 12 and detector 14, as well as the injecting direction of the source 12 and the receiving direction of the detector 14.

The intensity data which are detected and collected are processed via an inverse computation module 16 using a novel fast hybrid dual Fourier reconstructing algorithm to produce a three-dimensional image map of the internal structure of the turbid medium 30. The reconstruction algorithm (which is utilized by the inverse computation module 16) includes a forward physical model 20. The forward model 20 (which is discussed in further detail below) describes photon migration (light propagation) in the turbid medium in accordance with optical parameters characteristic of a turbid medium: scattering rate, absorption rate, and, possible, differential angular scattering rate. The forward model 20 is based on an analytical solution 22 to the Boltzmann photon transport equation, or its diffusion approximation. Specifically, the analytical solution 22 comprises a cumulate solution of the Boltzmann photon transport equation or a diffusive solution in an infinite uniform medium and a corresponding solution in a slab uniform medium, by adding virtual sources. The analytical solution 22 serves as the background Green's function of the forward physical model 20 for the present tomographic method.

An inverse algorithm module 18, which employs a novel hybrid-dual-Fourier inverse algorithm, unique to the present imaging method, generates an internal map of the turbid medium by reconstructing the turbid medium structure. The inverse process is discussed below in further detail.

The reconstruction algorithm of the present invention includes a regularization module 24 that provides suitable regularization parameters for use by the inverse algorithm module 18. Conventional methods such as the L-curve method disclosed in "The Truncated SVD as a Method of Regularization," by Hansen, BIT, 17, 354–553, 1987, and the generalized cross validation (GCV) method disclosed in "Generalized Cross-Validation as a Method for Choosing a Good Ridge Parameter", by Golub et al., Technometrics, 21, p. 215–223 (1979), may be used in the regularization module 24 for providing suitable regularization parameters. These methods disclosed in these references are incorporated herein by reference.

The system 10 may also include a knowledge catalog system 26 for building a relationship between different tissue structures and their corresponding optical parameters at different wavelengths of light source. The catalog system 26 is utilized by the inverse computation module 16 to determine the local tissue structure and refine the corresponding optical parameters at a position. This system 26 can be utilized to determine the local material structure by distinguishing or determining the local material structure from the local optical parameters.

The reconstruction algorithm of the system 10 also includes an image graphic display module 28 for generating and displaying 3-D reconstructed images.

It is to be understood that the present system and method is preferably implemented on a fast speed computer, for example, PC or Silicon Graphic (SGI), for fast numerical computation and graphic display.

It is to be further understood that the present system and method may be used to image various highly scattering turbid media such as biological plant tissue, animal tissue, and human tissue. With regard to human tissue, for example, the present invention can be utilized to image breasts, brain, prostate, arteries, liver, kidney, bones in joints, calcification regions, and arthritis, fingers, arms, legs, feet, etc. The turbid media, inside or through which the objects may be imaged, also includes cloud, fog, smog, dust, smoke, etc, as well as defects in semiconductors, ceramics, dielectrics, corrosion under paint.

Inverse Algorithm

A novel hybrid dual Fourier inverse reconstruction algorithm is developed based on the present inventor's discovery, that by performing a dual Fourier transform upon both arguments related to the source positions and the detector positions, and using a linear hybrid transform, 3D tomography can be realized for case of multiple sources and multiple detectors.

Figure 1:
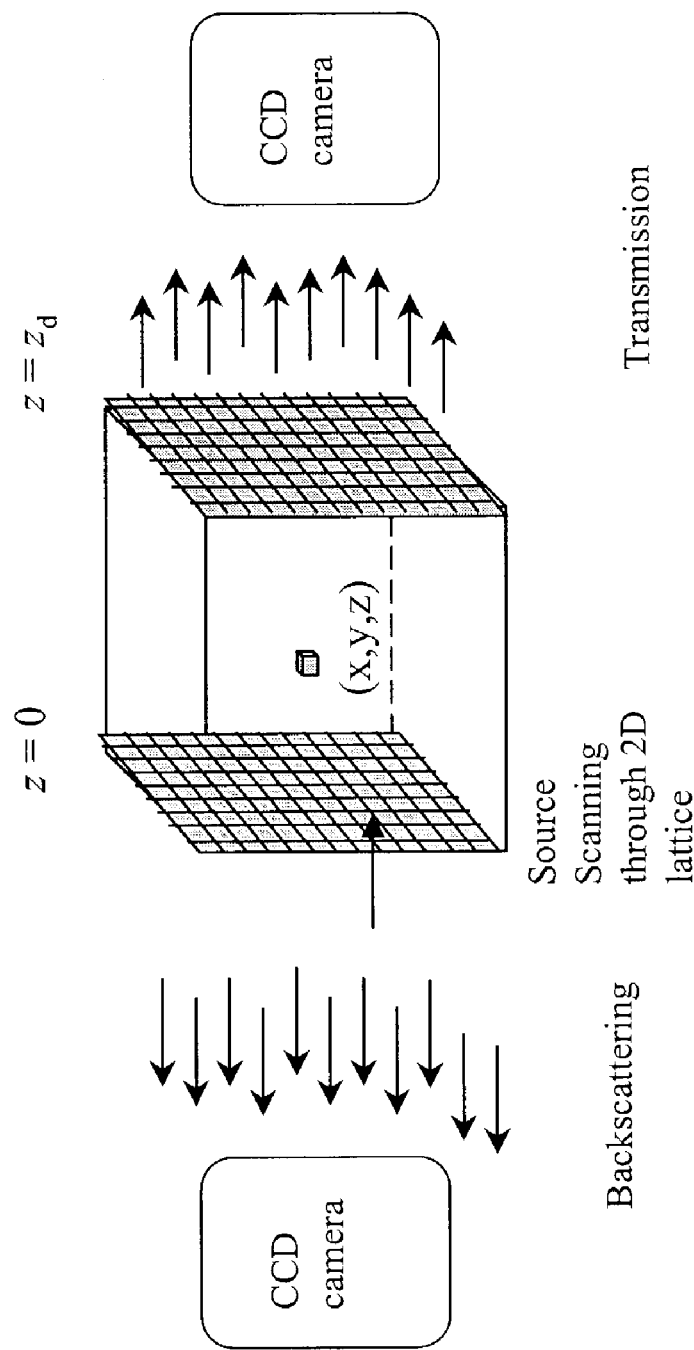
FIG. 1 is a simplified schematic view of device for detecting breast cancer in parallel geometry using the hybrid-dual-Fourier tomographic algorithm of the present invention.
Figure 2:
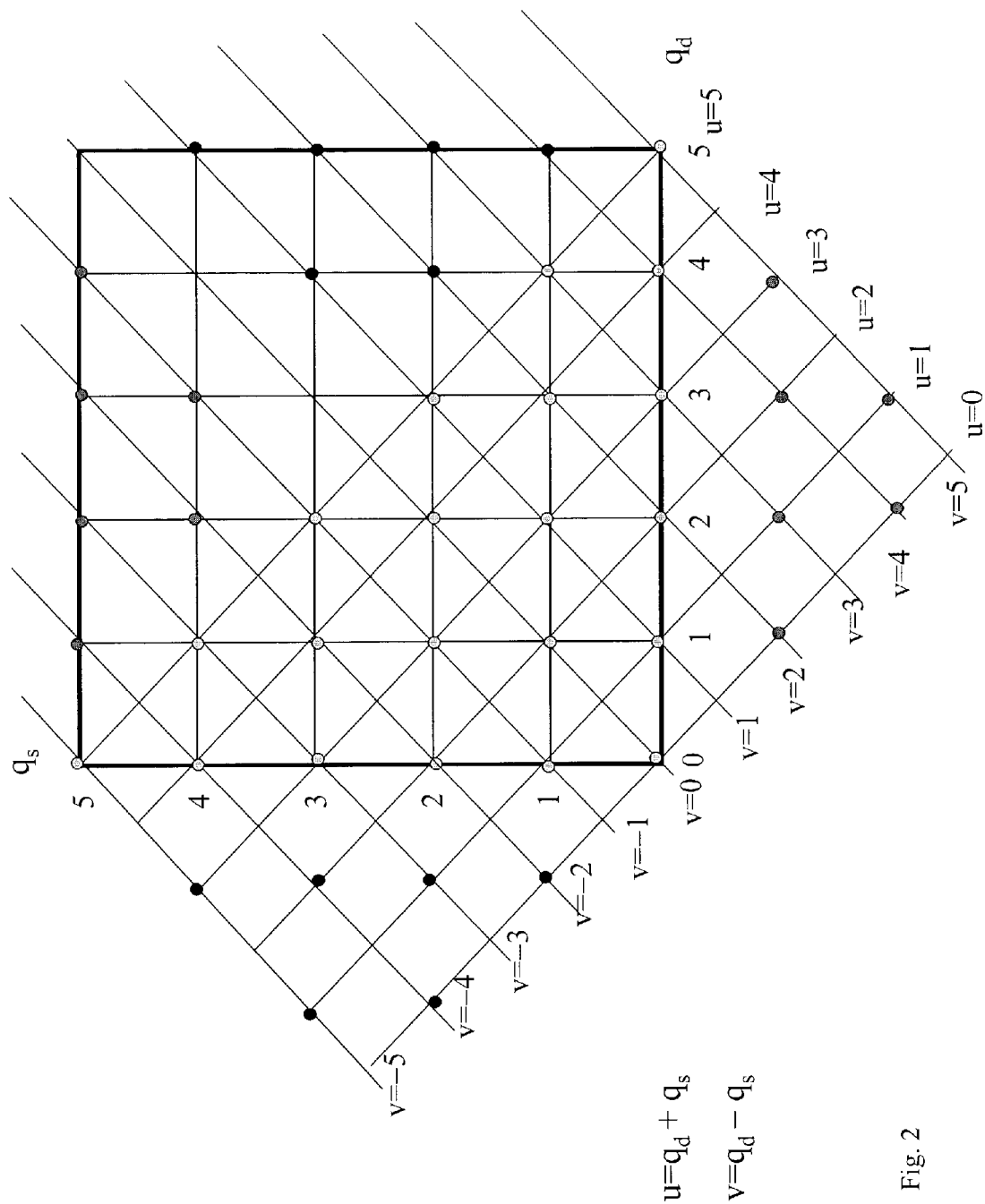
FIG. 2 is a diagram for explaining the linear hybrid transform using an example of 6×6 lattices from ($q_d$, $q_s$) coordinates to (u, v) coordinates of the present invention.
Figure 3:
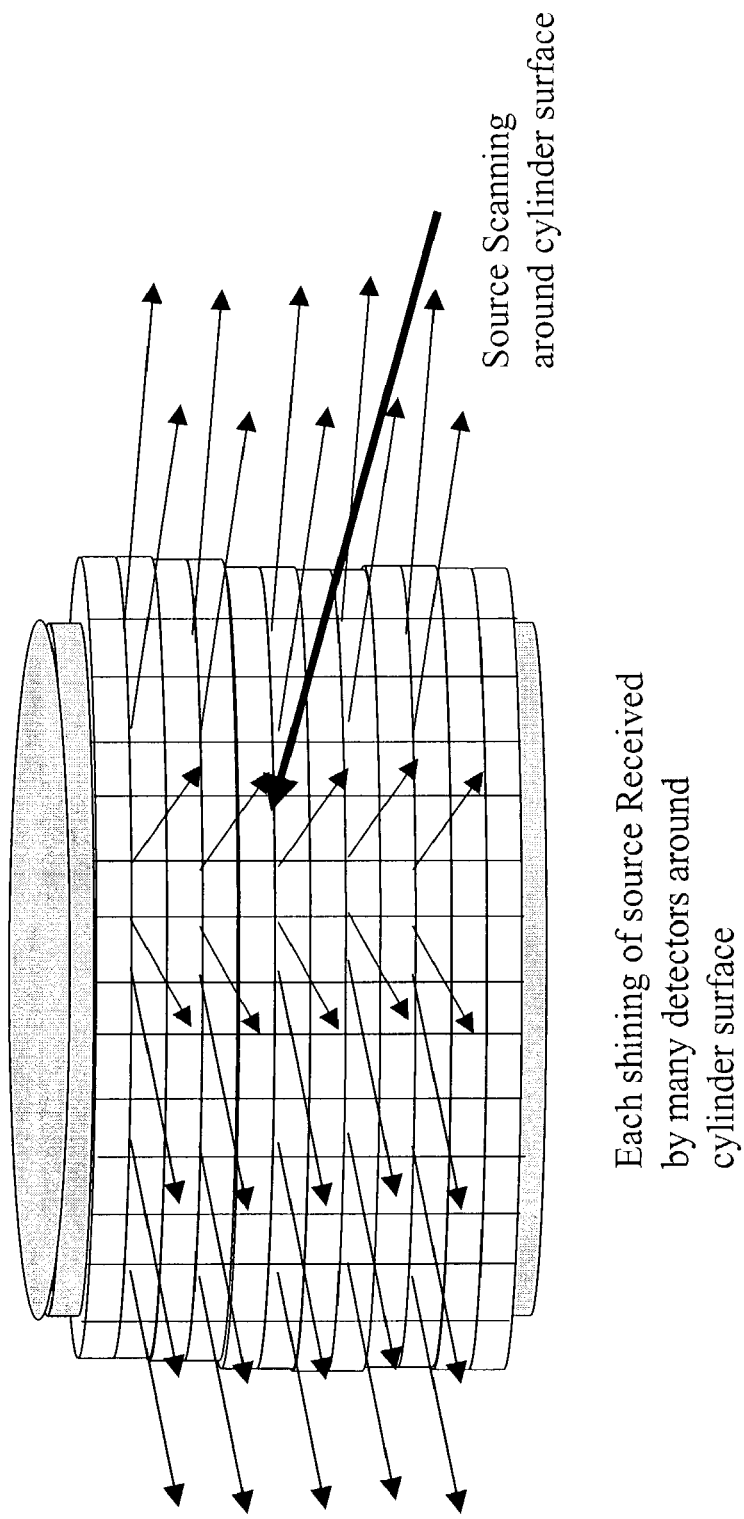
FIG. 3 is a simplified schematic view of device for detecting breast cancer in cylinder geometry using the hybrid-dual-Fourier tomographic algorithm of the present invention.

The formula for the parallel geometry is presented in equation (1) to equation (4) in the section "summary of the invention." FIG. 2 schematically explains the linear hybrid transform in equation (3), using an example of 6×6 lattices from $(q_d, q_s)$ coordinates to $(u, v)$ coordinates. Note that the periodic property of lattices in the Fourier space is used, for example, $\hat{Y}(u=2, v=4)=\hat{Y}(q_d=3, q_s=5)$ as shown in FIG. 2. This figure shows that $\hat{Y}$ and $\hat{W}$ at each node in $(u, v)$ coordinates can be obtained, respectively, from $\hat{Y}$ and $\hat{W}$ at the corresponding node in $(q_d, q_s)$ coordinates without any algebraic manipulation.

The inverse formula can be written as $$\tilde{X}=\tilde{Y}^T\tilde{W}[\tilde{W}^T\tilde{W}+\Lambda]^{-1}, \text{ For each } \vec{u}, \qquad (9)$$

which inverses a matrix $\tilde{W}^T\tilde{W}$ with $N_z$ rank, where $N_z$ is number of 1D division along z layer. In equation (9), $\Lambda$ is the regularization matrix. Examples of references which disclose the regularization technique include: R. R. Alfano et al. "Time-resolved diffusion tomographic 2D and 3D imaging in highly scattering turbid media," U.S. Pat. No. 5,931,789, issued Aug. 3, 1999; U.S. Pat. No. 6,108,576, issued Aug. 22, 2000, all of which are incorporated herein by reference.

After $\tilde{X}(\vec{u}, z)$ for all $\vec{u}$ are obtained, a 2D inverse Fourier transform produces $X(\vec{r}, z)$, which is the 3D image of optical parameters. By use of the abovementioned procedure of tomography, 3D imaging is realized for multiple-sources and multiple-detectors in the parallel geometry. Using this algorithm to perform an inverse reconstruction of 3D image of breast tissue with enough fine resolution (for example, 32×32×20 voxels) only takes a few minutes on a personal computer.

The formula for the cylinder geometry is presented in equation (5) to equation (8) in the section "summary of the invention". In this case, a 1D dual Fourier transform is performed along z direction, and the matrix $\tilde{W}^T\tilde{W}$ in equation (9), which should be inversed, has $N_{xy}$ rank, where $N_{xy}$ is number of 2D division at x-y plane.

Forward Physical Model

Forward Model Based on the Solution of the Radiative Transfer Equation

The following discussion provides the theoretical basis for the forward model of the present invention. The structure of a highly scattering turbid medium can be characterized by the following optical parameters: $\mu_s(r)$ the scattering rate; $\mu_a(r)$ the absorption rate; and $\mu_s(r)P(s',s,r)$ the differential angular scattering rate. Hereafter r denotes a 3D vector. These parameters are position dependent, and represent the non-uniform structure of the highly scattering turbid medium. The values of these optical parameters vary using light sources with different wavelengths, $\lambda$. For instance, the absorption rate, $\mu_a(r)$ will vary with the wavelength because the absorption peak appears when the wavelength matches the difference of the energy levels of a specific molecular structure. In addition, the scattering rate, $\mu_s(r)$, and the differential angular scattering rate, $\mu_s(r)P(s',s,r)$ vary with the wavelength because these rates are related to $R/\lambda$, where R is the average radius of the scatterer.

The photon propagation in a medium is described by the photon distribution function, $I(r,s,t)$, namely, the photon intensity in a unit of solid angle as functions of time t, position r, and direction s. The mathematical equation governing photon propagation is the well-known Boltzmann radiative transfer equation:

$$\partial I(r,s,t)/\partial t + cs\cdot\nabla_r I(r,s,t) + \mu_a(r)I(r,s,t) = \mu_s(r)\int P(s,s',r)[I(r,s't)-I(r,s,t)]ds' + \delta(r-r_0)\delta(s-s_0)\delta(t-0) \qquad (10)$$

It is difficult to directly solve the above radiative transfer equation. A perturbation method is used which designates the photon distribution function in a uniform background medium as the zero-order approximation. This method designates, as the first-order perturbation, the change of the photon distribution function due to the change of optical parameters compared to that in the uniform background medium. The change of scattering and absorption parameters are defined as follows:

$$\Delta\mu_s(r)=\mu_s(r)-\mu_s^{(0)};$$

$$\Delta\mu_a(r)=\mu_a(r)-\mu_a^{(0)}; \text{ and}$$

$$\Delta[\mu_s P](s',s,r)=\mu_s(r)P(s',s,r)-\mu_s^{(0)}P^{(0)}(s',s); \qquad (11)$$

where the quantities with super index (0) are the optical parameters in a uniform background medium (a medium without hidden objects). By expanding $\Delta[\mu_s P](s',s,r)$ in Legendre polynomials, we get:

$$\Delta[\mu_s P](s',s,r) = \frac{1}{4\pi}\sum_l \Delta\mu_s(r)\Delta a_l(r)P_l[\cos(s's)] \qquad (12)$$

with normalization of $\Delta a_0(r)=1$. The corresponding Legendre coefficients, $\Delta\mu_s(r)\Delta a_l(r)$ can also serve as optical parameters. The following equation based on the standard Born approximation method represents our forward model:

$$\Delta I(r_d,s_d,t|r_s,s_s) = \int dt' \int dr \int ds\, T^{(0)}(r_d,s_d,t-t'r,s')\{\int \Delta[\mu_s P](s',s,r)I^{(0)}(r,s,t'|r_s,s_s)ds - [\Delta\mu_s(r)+\Delta\mu_a(r)]I^{(0)}(r,s', t'|r_s,s_s)\} \qquad (13)$$

where $\Delta I\ (r_d,s_d,t|r_s,s_s)$ is the change in light intensity received by a detector located at $r_d$, along the direction $s_d$, and at time t, which is injected from a source located at $r_s$, along a direction of $s_s$, at time t=0. The word "change" refers to the difference in intensity compared to that received by the same detector, from the same source, but light passing through a uniform background medium (i.e., a medium without hidden objects). The term $I^{(0)}$ ($r_2,s_2,t|r_1,s_1$) is the intensity of light located at $r_2$ along the direction $s_2$ an at time t, which is injected from a position $r_1$ along a direction of $s_1$ at time t=0 migrating in a uniform background medium. Examples of references which disclose technique for obtaining $I^{(0)}$ ($r_2,s_2,t|r_1,s_1$) in an infinite uniform medium include: "W. Cai, et al., "Cumulant solution of the elastic Boltzmann transport equation in an infinite uniform medium", Phys. Rev. E. 61 3871 (2000), W. Cai, et al., "Analytical solution of the elastic Boltzmann transport Equation in an infinite uniform medium using cumulant expansion", J. Phys. Chem. B104 3996 (2000), W. Cai, et al., "Analytical solution of the polarized photon transport equation in an infinite uniform medium using cumulant expansion," Phys. Rev. E 63 016606 (2001), which are incorporated herein by reference. Examples of references which disclose technique for obtaining $I^{(0)}$ ($r_2,s_2,t|r_1,s_1$) in an semi-infinite and slab shaped uniform medium include: R. R. Alfano et al., "Time-resolved optical backscattering tomographic image reconstruction in scattering media", U.S. Pat. No. 6,205,353 issued Mar. 20, 2001, which is incorporated herein by reference.

We expand the background Green's function in spherical harmonics:

$$I^{(0)}(r, s, t'|r_s, s_s) = \sum_{l,m} A_{lm}(r, r_s, s_s, t') Y_{lm}^{(e)}(s) + B_{lm}(r, r_s, s_s, t') Y_{lm}^{(o)}(s),$$

$$I^{(0)}(r_d, s_d, t - t'|r, s') = \sum_{l,m} C_{lm}(r, r_d, s_d, t - t') Y_{lm}^{(e)}(s') + D_{lm}(r, r_d, s_d, t - t') Y_{lm}^{(o)}(s'),$$

where $$Y_{lm}^{(e)}(\theta, \phi) = P_l^{(m)}(\cos\theta)\cos(m\phi)$$

and $$Y_{lm}^{(o)}(\theta, \phi) = P_l^{(m)}(\cos\theta)\sin(m\phi),$$

with $$P_l^{(m)}(\cos\theta)$$

the associated Legendre function. The spherical transform is performed using a fast Fourier transform for the integral over $\phi$, and a Clenshaw-Curtis quadrature for the integral over $\theta$.

Using the orthogonality relation of the spherical function and the addition theorem:

$$\sum_m Y_{lm}(s) Y_{lm}^*(s') = P_l[\cos(s \cdot s')],$$

the analytical integration over s and s' in Eq. (13) can be performed. For time resolved data, the contribution from an absorbing object located at $r_k$ is given by $$\Delta I(r_d, s_d, r_s, s_s, t|r_k) = -\Delta\mu_a(r_k)\delta V_k \int_0^t dt' \quad (15)$$

$$\sum_{l=0}^{L} \frac{4\pi}{(2l+1)} \sum_m A_{lm}(r_k, r_s, s_s, t') C_{lm}^*(r_k, r_d, s_d, t - t')$$

where $\delta V_k$ is the volume of $k^{th}$ voxel, and L is the cut-off value in the Legendre expansion in Eq. (15). The contribution from a scattering object located at $r_k$ is given by $$\Delta I(r_d, s_d, r_s, s_s, t|r_k) = \quad (16)$$

$$-\delta V_k \int_0^t dt' \sum_{l=1}^{L} \frac{4\pi}{(2l+1)} \left[ \Delta\mu_s(r_k)\left(1 - \frac{a_l^{(0)}}{2l+1}\right) - \mu_s^{(0)} \frac{\Delta a_l(r_k)}{2l+1} \right]$$

$$\sum_m A_{lm}(r_k, r_s, s_s, t') C_{lm}^*(r_k, r_d, s_d, t - t')$$

For Frequency domain (or CW) data, the contribution from an absorbing object located at $r_k$ is given by $$\Delta I(r_d, s_d, r_s, s_s, \omega|r_k) = \quad (17)$$

$$-\Delta\mu_a(r_k)\delta V_k \sum_{l=0}^{L} \frac{4\pi}{2l+1} \sum_m A_{lm}(r_k, r_s, s_s, \omega) c_{lm}^*(r_k, r_d, s_d, \omega),$$

and the contribution from a scattering object located at $r_k$ is given by $$\Delta I(r_d, s_d, r_s, s_s, \omega|r_k) = -\delta V_k \sum_{l=1}^{L} \frac{4\pi}{2l+1} \left[ \Delta\mu_s(r_k)\left(1 - \frac{a_l^{(0)}}{2l+1}\right) - \mu_s^{(0)} \frac{\Delta a_l(r_k)}{2l+1} \right] \quad (18)$$

$$\sum_m A_{lm}(r_k, r_s, s_s, \omega) c_{lm}^*(r_k, r_d, s_d, \omega).$$

By replacing $Y=[\Delta I/I^{(0)}]$ by $-\ln[I/I^{(0)}]$), our model, to some extent, automatically includes higher order non-linear contribution. This procedure is usually called the Rytov approximation.

A simplified photon-transport forward model has been developed. An example of references which disclose technique to obtaining this forward model includes: M. Xu et al: "Photon-transport forward model for imaging in turbid media," Opt. Lett. 26, 1066–1068 (2001), which is incorporated herein by reference.

Forward Model Based on the Solution of the Diffusion Equation

By making Legendre expansion of the Boltzmann equation (10) and cut at the lowest order, a diffusion equation is obtained as an approximate equation of radiative transfer:

$$\left[\frac{\partial}{\partial t} + c\mu_a(r) - \nabla(cD(r)\nabla)\right]N(r, t) = S(r, t) \quad (19)$$

Where N(r,t) is the photon density, D(r) is the diffusive coefficient, and S(r,t) is the source distribution. The corresponding equation for cases of steady state and frequency-domain can easily derived from equation (19).

Under first-order perturbation, the change of the photon density is determined from the change of optical parameters compared to that in the uniform background medium. The change of scattering and absorption parameters are defined as follows:

$\Delta D(r) = D(r) - D^{(0)}$;

$\Delta \mu_a(r) = \mu_a(r) - \mu_a^{(0)}$. \quad (20)

The corresponding forward model for the time-resolved case is given by $$\Delta N(r_d, r_s, t) = \int dr c\Delta\mu_a(r) \int d\tau G^0(r_d, r, t-\tau) G^0(r_s, r, \tau) - \quad (21)$$

$$\int dr\Delta D(r) \int_0^t d\tau \nabla G^0(r_d, r, t-\tau) \cdot \nabla G^0(r_s, r, \tau)$$

The time-resolved Green's function in an infinite uniform background medium is:

$$G^0(r, t) = \frac{1}{(4\pi D^{(0)} ct)^{3/2}} \exp\left[-\frac{(x^2 + y^2 + z^2)}{4D^{(0)} ct}\right] \exp(-\mu_a^{(0)} t) \quad (22)$$

The corresponding forward model for the frequency-domain case is given by $\Delta N(r_d,r_s,\omega) = \int dr c\Delta\mu_a(r)G^0(r_d,r,\omega)G^0(r_s,r,\omega) - \int dr\Delta D$
$(r)\nabla G^0(r_d,r,\omega)\cdot\nabla G^0(r_s,r,\omega)$ \quad (23)

The frequency-domain Green's function in an infinite uniform background medium is:

$G^0(r,\omega) = \exp\{[(c\mu_a^{(0)} + i\omega)/D^{(0)}]^{1/2}|r|\}/(4\pi D^{(0)}|r|)$ \quad (24)

Equations (22) and (24) can be extended to semi-infinite and slab medium by introducing the corresponding "image" sources. Equation (21) and (23) provide the needed weight function in equation (1) in the diffusion forward model.

Experimental Design for Image of Breast

Figure 5:
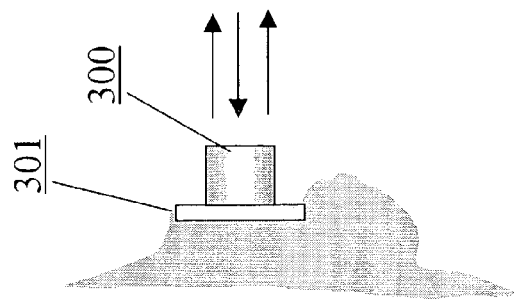
FIGS. 5a, 5b, and 5c are simplified schematic views of devices for detecting breast cancer using the hybrid-dual-Fourier tomography method in parallel geometry of the present invention.
Figure 5:
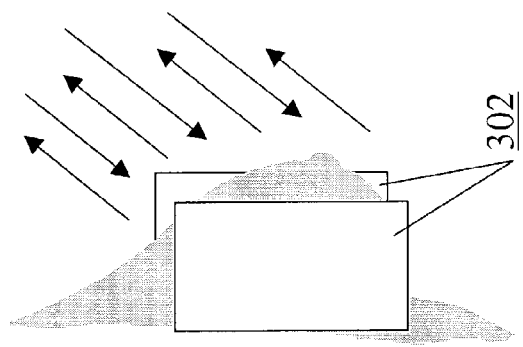
Figure 5:
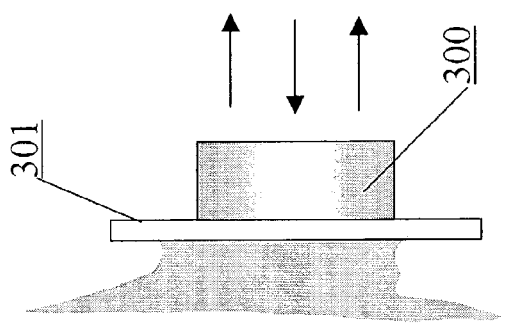

Referring now to FIG. 5, experimental devices are shown which may be utilized for detecting breast cancer using optical tomography method in parallel geometry of the present invention. As shown in FIG. 5(*a*), a sources-detector head 300, which includes a 2D array of sources and detectors, is fixed on a transparent plate 301. A medical doctor using a hand or other method (for example, moving the patient's bed) can press the plate 301 against a patient's breast to push the breast against the chest wall. Thereafter, a laser can be applied, and the detectors can then receive backscattered light signals. From these signals, through numerical computation by computer using the hybrid dual Fourier tomography algorithm of the present invention, a three-dimensional image of the entire breast can be reconstructed. Since breast is soft and flexible, it is possible to squeeze a breast to about 2 cm to 4 cm above the chest. In another embodiment as shown in FIG. 5(*b*), the breast may be squeezed between two parallel transparent plates 302. In addition, the embodiment shown in FIG. 5(*c*) can be used to detect a local breast region near the sources-detectors. The embodiment of FIG. 5*c* is similar to that shown in FIG. 5(*a*), but the source-detector head 300 and the plate 301 are smaller. By pushing successively upon different areas of the breast, a test of the entire breast can be completed. In order to reduce the clinic time, data acquisition can be performed during the visit with a patient. The image reconstruction then can be computed in parallel during the patient's waiting time. If a near real-time image reconstruction can be realized, the doctor may also see an image of the local region of patient's breast immediately after the laser beam is applied. Since only a local region of the breast is compressed (using the embodiment of FIG. 5*c*), it is possible to push down the local region of breast to 1 cm to 2 cm above the chest wall using a moderate pressure. The advantage for the embodiments of FIGS. 5(*a*) and 5(*b*) is that the image of whole breast can be reconstructed at one time, hence, the clinic is fast. The embodiment of FIG. 5(*c*), on the other hand, can enhance the image resolution and can reduce pain because only a local region of breast is tested at a particular time.

Multiple Wavelengths

Figure 6:
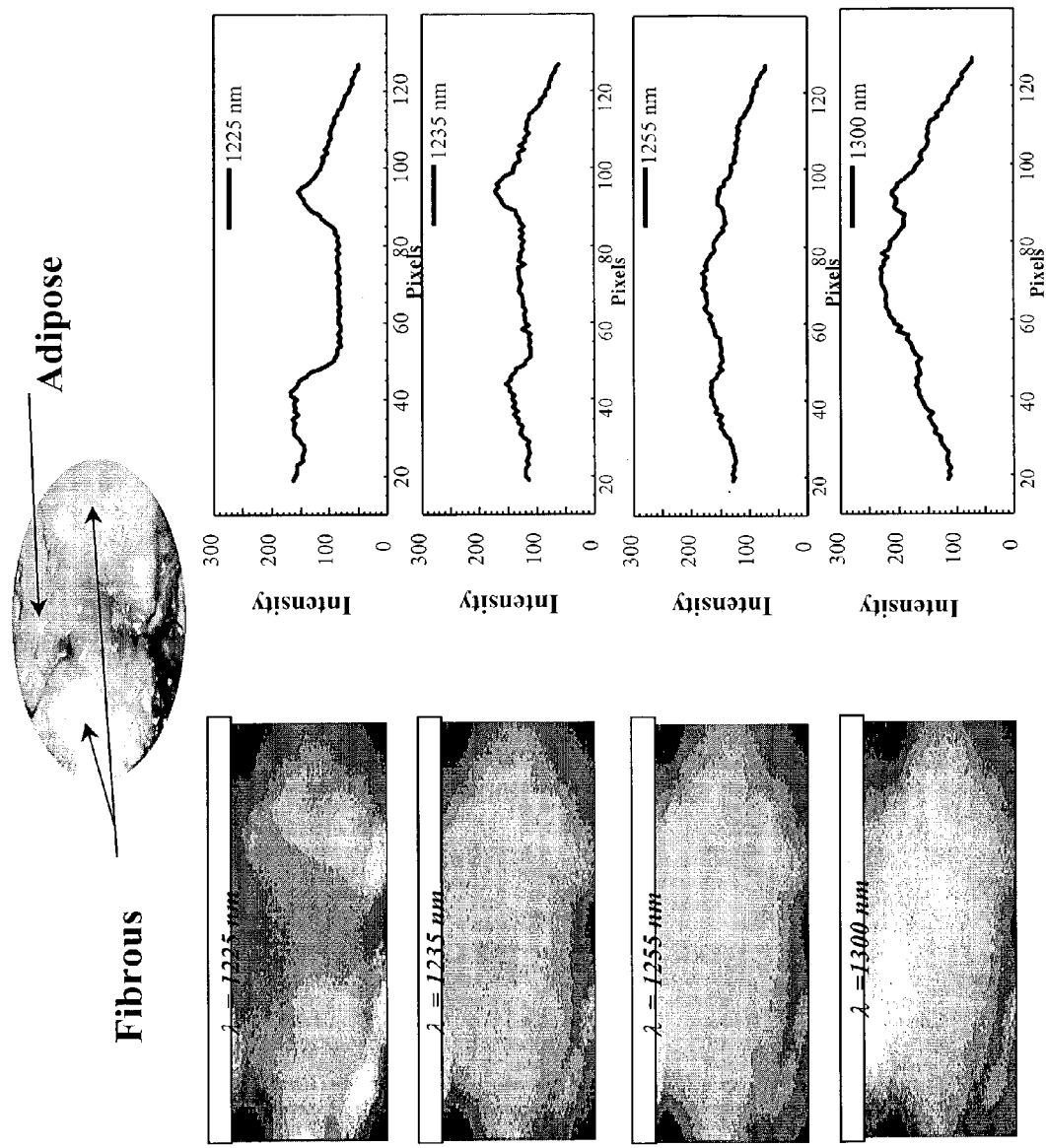
FIG. 6 is a diagram of transillumination images of a 5 mm thick human breast tissue sample comprising adipose and fibrous regions obtained using light of different wavelengths: (a) 1225 nm, (b) 1235 nm, (c) 1255 nm, and (d) 1300 nm from a Cr:forsterite laser. This figure is taken from the reference: S. K. Gayen et al., "Near-infrared laser spectroscopic imaging: a step towards diagnostic optical imaging of human tissues", Lasers in the Life Sciences Vol. 8 187 (1999).
Figure 7:
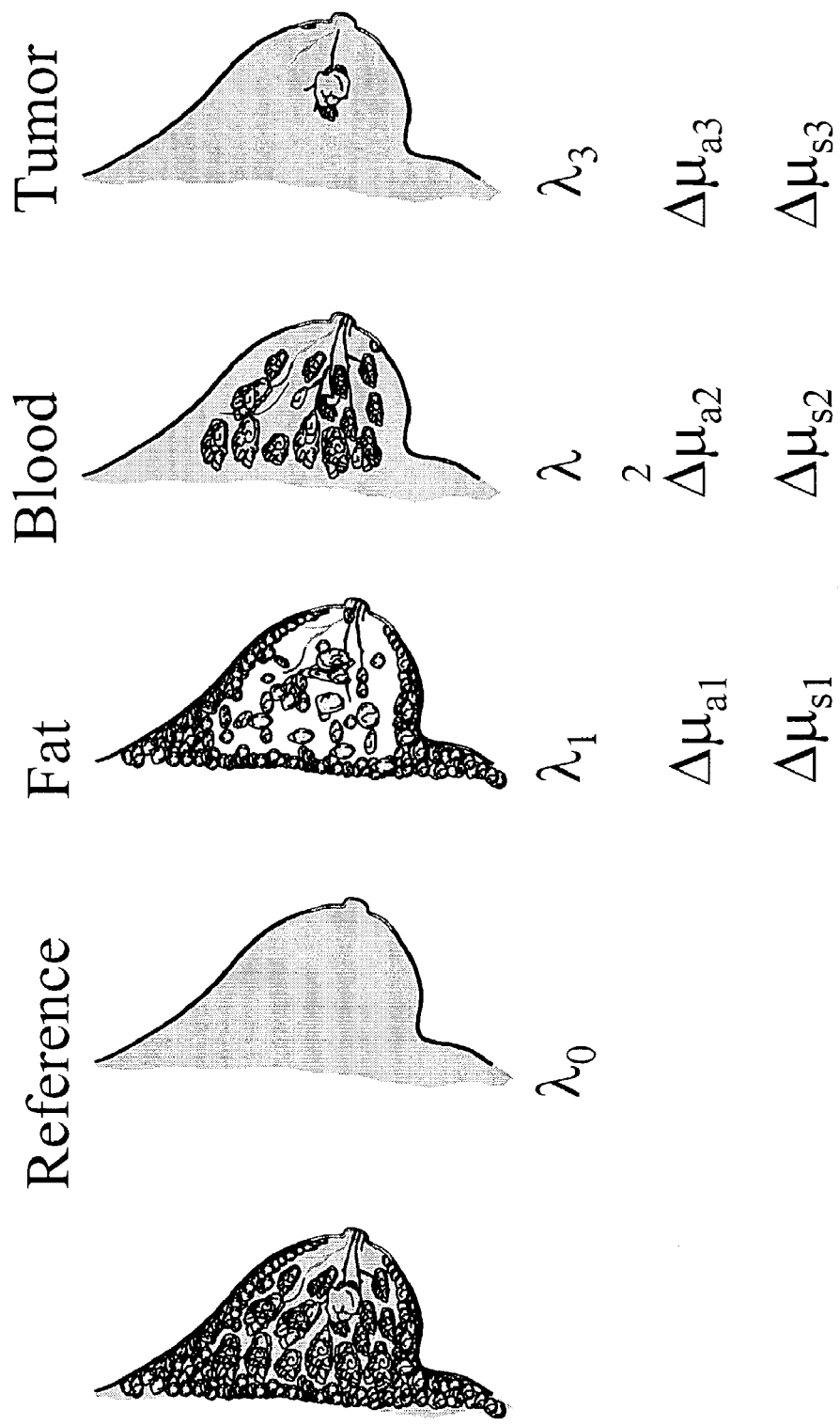
FIG. 7 is a schematic diagram illustrating image maps of key components of breast tissue using different wavelengths.

Advantageously, this system can determine the local material structure by distinguishing different values of optical parameters obtained using different light wavelengths. FIG. 6 shows the experimental images of transmission light from a human breast tissue sample, comprising adipose and fibrous regions, with light sources at different wavelengths. Publication which discloses this result includes S. K. Gayen et al., "Near-infrared laser spectroscopic imaging: a step towards diagnostic optical imaging of human tissues", Lasers in the Life Sciences Vol. 8 187 (1999), which is incorporated herein by reference. The absorbing coefficient and the scattering coefficient through a type of tissue has different values with a laser source of different wavelengths. When two sources are used having wavelengths $\lambda_0$ and $\lambda_1$, where $\lambda_0$ is a non-characteristic wavelength, the difference of their absorption coefficients $\mu_a(r,\lambda_1)-\mu_a(r,\lambda_0)$ and the difference of scattering coefficients $\mu_s(r,\lambda_1)-\mu_s(r,\lambda_0)$ obtained by our inverse computation shows a more clear image map where the hidden object is located by eliminating the background values. This procedure of using different $\lambda$ can yield maps of water, blood, and calcification, cancer, precancerous and benign tissue. A schematic diagram for using the different wavelengths in obtaining the internal maps of different components in a breast is shown in FIG. 7.

Test of Hybrid Dual Fourier Imaging Method Using Simulating Data

As a proof of the concept of the hybrid-dual-Fourier tomographic algorithm, a 3D image reconstruction is performed from simulated data using the diffusion forward model.

3D Image in Parallel Geometry Using Hybrid-Dual-Fourier Tomographic Method

Figure 8:
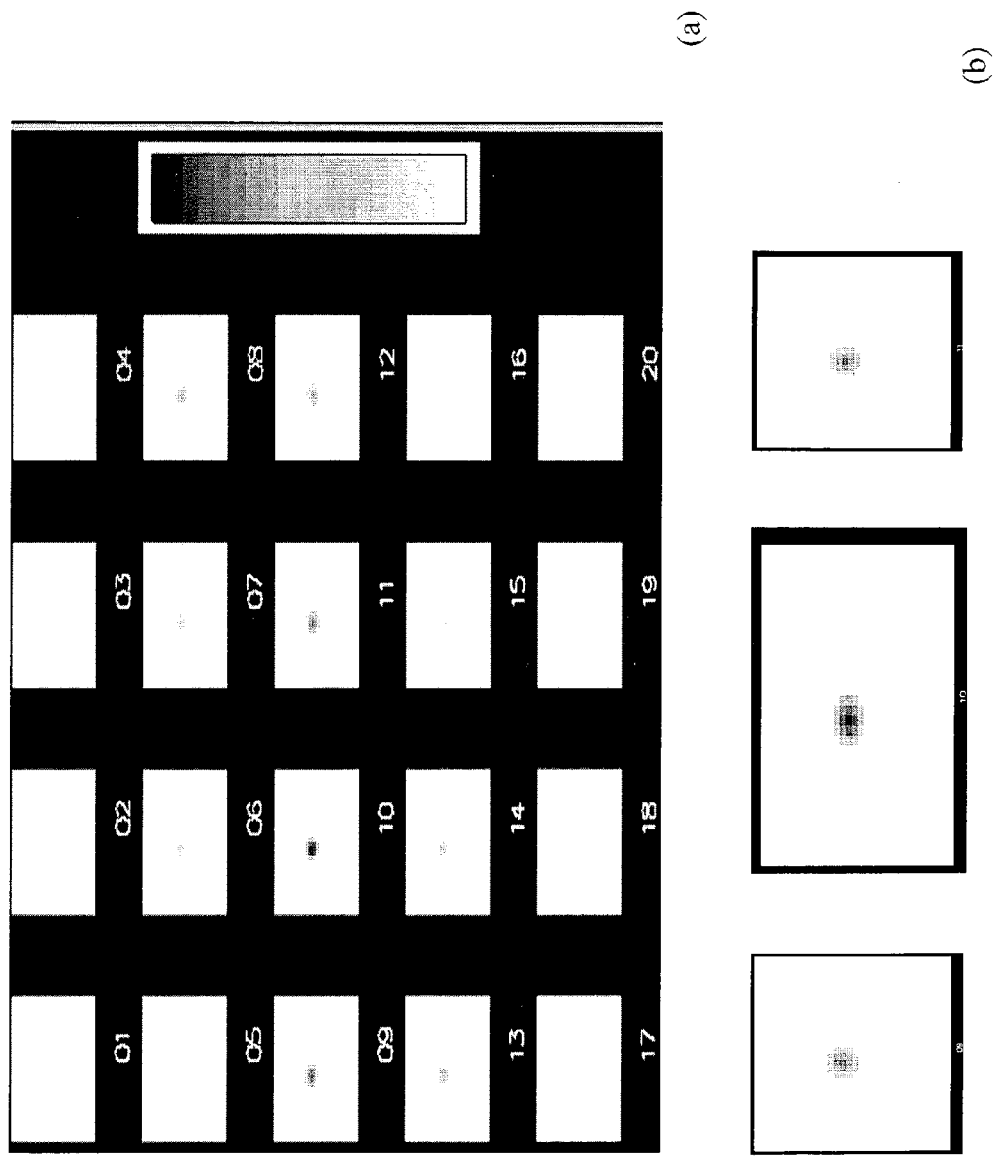
FIG. 8 is a diagram of comparative 3D images of a hidden absorbing object located at position (15, 15, 10) inside of a turbid medium divided into 32×32×20 voxels reconstructed by hybrid dual Fourier tomography in transmission parallel geometry based on the diffusion forward model.

A slab turbid medium with the optical parameters of breast, the transport mean free path $l_t=1$ mm, the absorption length $l_a=300$ mm, and thickness $z_d=40$ mm, is divided into 20 layers. A CW laser shines, step by step, through a 32×32 2D array on the $z_s=0$ plane, each shining light passes through the medium and is received by a 32×32 2D array of detectors on the $z_d=40$ mm plane. The medium is divided into 32×32×20 voxels, each 3×3×2 mm³. A hidden object, with absorption length $l_a=50$ mm and volume 3×3×2 mm³, is located at position labeled (15, 15, 10). The tomographic images are shown in FIG. 8 using the new algorithm and hybrid transform. The number at FIG. 8a labels the z layers counting form source to the detector (each layer is separated by 2 mm). The FIG. 8b is the amplified figures of 9$^{th}$, 10$^{th}$, 11$^{th}$ layers. The simulated results show that the obtained image has maximum value of absorption coefficient at the correct 3D position of the object (15,15,10). At the nearest neighbor in x-y lattice (15, 14, 10) or (15, 16, 10) etc., the values of absorption coefficient decrease about 20%, and then further decrease to about 50% at (15, 13, 10) etc., which indicates the resolution is about 6 mm in the transverse x-y plane. Comparing the values of the absorption coefficient at voxels (15, 15, 9) and (15,15,11) with (15, 15, 10), we see that they decrease about 20%, and further decrease to about 50% at (15, 15, 8) etc. Since each layer is separated by 2 mm, the resolution along z direction is about 6 mm. In general, the axial resolution (along z direction) is poorer than lateral resolution [at (x, y) plane]. In the parallel transmission geometry, two Green's functions in the weight function compensate each other when the z position of the hidden object changes, which leads to a poor sensitivity of photon intensity to the z position of the object.

The embodiments of the present invention described above are intended to be merely exemplary and those skilled in the art should be able to make numerous variations and modifications to it without departing from the spirit of the present invention. All such variations and modifications are intended to be within the scope of the present invention as defined in the appended claims.

We claim:

1. A method for producing a three-dimensional image of objects in a turbid medium from a hybrid dual Fourier transform, comprising:
    (a) measuring intensity data at multiple detectors from multiple sources in parallel geometry;
    (b) transforming data at positions of the detectors and the sources into Fourier coordinates ($q_d$, $q_s$) to create a dual two-dimensional x-y spatial Fourier transform;
    (c) performing a linear hybrid transformation of the Fourier coordinates ($q_d$, $q_s$) of the multiple sources and multiple detectors in accordance with a predefined relationship;
    (d) performing a one-dimensional inverse reconstruction for each first value of the predefined relationship; and
    (e) generating a fast two-dimensional inverse Fourier transform based on each first value to produce three-dimensional image of objects in the turbid medium.

2. The method of claim 1, wherein said predefined relationship comprises the following relationship:

$$\vec{u} = \vec{q}_d + \vec{q}_s$$
$$\vec{v} = \vec{q}_d - \vec{q}_s;$$

wherein $\vec{u}$ and $\vec{v}$ are coordinates, and $q_d$, $q_s$ are the Fourier coordinates of the multiple sources and multiple detectors, respectively.

3. The method of claim 1, wherein said each first value is $\vec{u}$ of the following relationship:

$$\vec{u} = \vec{q}_d + \vec{q}_s$$
$$\vec{v} = \vec{q}_d - \vec{q}_s;$$

wherein $\vec{u}$ and $\vec{v}$ are coordinates, and $q_d$ and $q_s$ are the Fourier coordinates of the multiple sources and multiple detectors, respectively.

4. The method of claim 1, wherein said predefined relationship comprises the following relationship:

$$u = q_d + q_s$$
$$v = q_d - q_s;$$

wherein u and v are coordinates, and $q_d$ and $q_s$ are the Fourier coordinates of the multiple sources and multiple detectors, respectively.

5. The method of claim 1, wherein said each first value is u of the following relationship:

$$u = q_d + q_s$$
$$v = q_d - q_s;$$

wherein u and v are coordinates, and $q_d$ and $q_s$ are the Fourier coordinates of the multiple sources and multiple detectors, respectively.

6. The method of claim 1, wherein computational burdens of image reconstruction are reduced by combining a dual two-dimensional Fast Fourier Transform inversion with a one-dimensional matrix inversion.

7. The method of claim 1, further comprising the step of:
    performing the linear hybrid transform to provide a fast three-dimensional Fourier image reconstruction for multiple sources and multiple detectors.

8. The method of claim 1, wherein the multiple sources are selected from the group consisting of light, X-ray, micro-wave, sound, electrons, particles and mechanical vibration.

9. The method of claim 1, wherein the detectors comprise sensors for detecting signals of one of light, sound, electricity and mechanical waves.

10. The method of claim 1, wherein the intensity data is a function of a coordinate space selected from the group consisting of position, time, wavelength spectrum and vibration mode.

11. The method of claim 1, wherein a hybrid dual Fourier tomographic method is implemented for at least one of continuous-wave sources, frequency domain sources and ultra-fast pulse sources.

12. The method of claim 1, wherein steps (b) thru (e) are solved based on N-dimensional dual de-convolution.

13. The method of claim 1, wherein the turbid medium has a cylindrical surface, and the multiple sources and multiple detectors are arranged circumferentially with respect to the cylinderical surface.

14. The method of claim 13, wherein the hybrid dual Fourier tomographic method for the cylindrical surface is performed in accordance with the following relationships $$Y(\vec{r}_d, \vec{r}_s, z_d, z_s) = \int d\vec{r}\, dz\, W(\vec{r}_d, \vec{r}_s, \vec{r}; z_d - z, z_s - z) X(\vec{r}, z);$$

wherein $W(\vec{r}_d, \vec{r}_s, \vec{r}; z_d - z, z_s - z)$ is a weight function, which is function of $z_d - z$ and $z_s - z$;

$$\hat{Y}(q_d, q_s, \vec{r}_d, \vec{r}_s) = \int dz\, \hat{W}(q_d, q_s, \vec{r}, \vec{r}_d, \vec{r}_s) \hat{X}(q_d + q_s, \vec{r})$$

wherein $\hat{Y}$, $\hat{X}$, and $\hat{W}$ are corresponding Fourier space quantities;

$$u = q_d + q_s$$

$$v = q_d - q_s;$$

wherein u and v are coordinates, and $q_d$, $q_s$ are the Fourier coordinates of the source and detector, respectively; and $$\tilde{Y}(u, v, \vec{r}_d, \vec{r}_s) = \int d\vec{r}\, \tilde{W}(u, v, \vec{r}_d, \vec{r}_s; \vec{r}) \tilde{X}(u, \vec{r});$$

wherein $\tilde{Y}$, $\tilde{X}$, and $\tilde{W}$ are, respectively, $\hat{Y}$, $\hat{X}$, and $\hat{W}$ as functions of u and v.

15. The method of claim 1, wherein a forward physical model of the method is based on an analytical cumulant solution to a Boltzmann photon transport equation.

16. The method of claim 15, wherein a background Green's function of the method comprises the cumulant solution of the Boltzmann photon transport equation.

17. The method of claim 15, wherein an accurate analytical form of a solution of the Boltzmann equation is implemented to permit computation of the forward physical model.

* * * * *